United States Patent [19]

Cosyns et al.

[11] Patent Number: 4,547,600

[45] Date of Patent: Oct. 15, 1985

[54] PROCESS FOR SELECTIVELY HYDROGENATING ACETYLENIC HYDROCARBONS OF A $C_4$ HYDROCARBON CUT CONTAINING BUTADIENE

[75] Inventors: Jean Cosyns, Maule; Jean-Paul Boitiaux, Paris, both of France

[73] Assignee: Societe Francaise des Produits pour Catalyse Pro-Catalyse, Rueil-Malmaison, France

[21] Appl. No.: 554,653

[22] Filed: Nov. 23, 1983

[30] Foreign Application Priority Data

Nov. 24, 1982 [FR] France ................................ 82 19835

[51] Int. Cl.$^4$ ................................................ C07C 5/02
[52] U.S. Cl. ..................................... 585/259; 585/258; 585/260
[58] Field of Search ......................... 585/258, 259, 260

[56] References Cited

U.S. PATENT DOCUMENTS

| | | | |
|---|---|---|---|
| 2,802,889 | 8/1957 | Freuel et al. ........................ | 585/259 |
| 2,927,141 | 3/1960 | Cohn ................................... | 585/258 |
| 3,221,078 | 11/1965 | Keith et al. .......................... | 585/258 |
| 4,409,410 | 10/1983 | Cosyns et al. ....................... | 585/259 |
| 4,484,015 | 11/1984 | Johnson et al. ..................... | 585/262 |

FOREIGN PATENT DOCUMENTS

| | | | |
|---|---|---|---|
| 2854698 | 6/1979 | Fed. Rep. of Germany ...... | 585/259 |
| 2036991 | 4/1969 | France . | |
| 2451352 | 11/1980 | France ............................... | 585/259 |
| 1263173 | 2/1972 | United Kingdom . | |

*Primary Examiner*—D. E. Gantz
*Assistant Examiner*—Chung K. Pak
*Attorney, Agent, or Firm*—Millen & White

[57] ABSTRACT

Process for the selective hydrogenation of the acetylenic hydrocarbons of a $C_4$ hydrocarbons cut, containing butadiene and at least 1% by weight of acetylenic hydrocarbons, without substantial hydrogenation of butadiene, wherein said hydrocarbons cut in liquid phase and hydrogen are contacted with a supported catalyst containing 0.05 to 0.5% by weight of palladium and 0.05 to 1% by weight of silver, the Ag/Pd ratio by weight being at least 0.7.

8 Claims, No Drawings

PROCESS FOR SELECTIVELY HYDROGENATING ACETYLENIC HYDROCARBONS OF A C₄ HYDROCARBON CUT CONTAINING BUTADIENE

BACKGROUND OF THE INVENTION

This invention relates to a process for the selective hydrogenation of acetylenic hydrocarbons of a hydrocarbon mixture containing diolefinic hydrocarbons.

The process for hydrocarbon conversion at high temperature, such as, for example, steam-cracking, produce unsaturated hydrocarbons such as, for example, ethylene, propylene, butadiene, butenes, together with hydrocarbons boiling in the gasoline range; the olefinic and diolefinic hydrocarbons having from 2 to 4 carbon atoms, obtained by this process, also contain a certain amount of acetylenic hydrocarbons. The content thereof varies according the severity of the conversion process but is always too low to make their separation and use as such in petrochemistry really attractive. However their presence in admixture with olefinic and diolefinic hydrocarbons makes it difficult or even impossible to use the latter in petrochemistry. This is, for example, the case of butadiene from which vinyl acetylene and butynes must be removed to the largest extent in order to make it suitable for elastomer production.

For removing the acetylenic hydrocarbons, various separation processes have been proposed, such as, for example, extractive distillation whereby hydrocarbons of different degrees of unsaturation can be separated. Thus, for example, in the case of the $C_4$ cut, it is possible to isolate the saturated compounds with 4 carbon atoms, the butenes, the butadiene and the acetylenic compounds. However, in order to obtain the desired purity, these processes require costly apparatuses and result, in addition, in a loss of yield due to the fact that the resultant hydrocarbons cut, containing a high proportion of acetylenic compounds, cannot be used in petrochemistry.

Other processes have been proposed to avoid these disadvantages; most of them consist of selectively hydrogenating the acetylenic compounds contained in the charge, for example a raw steam-cracking C₄ cut. A typical charge contains, by weight, from 20 to 60% of 1,3-butadiene, from 40 to 80% of butane, butenes and/or isobutene and from 0.1 to 0.5% of acetylenic compounds, comprising, for example, 0.05 to 0.2% of butyne and 0.1 to 0.4% of vinylacetylene. The French Pat. No. 2036991, for example, describes a process of this type.

The steady increase in the severity of steam-cracking (increase in the reaction temperature) resulted these last years in the production of cuts of much higher contents of acetylenic compounds, often of 1% or more by weight, for example, from 0.2 to 0.5% by weight of butynes and from 1 to 3% by weight of vinylacetylene. Such concentration of acetylenic hydrocarbons raise new problems for hydrogenation processes, in particular the problem of the quick deactivation of the catalyst due to formation and deposit of polymers and to the progressive dissolution of the active metals the rate of which is directly proportional to concentration of acetylenic hydrocarbons.

The problem of preparing stable catalysts for such reactions is not simple. For example, the French Pat. No. 1502462 shows that even in case of a charge containing a relatively low content acetylenic hydrocarbons, a catalyst of palladium on calcined alumina has already lost a large part of its activity and its selectivity after only 7 days of use. High palladium contents provide for a slight increase of the catalyst life time, but result in an excessively high cost of the catalyst.

SUMMARY

The object of the present invention is to overcome these disadvantages; a particular object is, for the treatment of C₄ cuts containing at least 1% by weight of acetylenic compounds, the use of catalysts which, although they contain only a small proportion of palladium, nevertheless exhibit an initial activity at least equal to that obtained with the known palladium catalyst or known palladium-silver catalyst, but which remain much more stable in the course of time.

In addition, with the use of these catalysts, the palladium content does not change appreciably during time even with charges having a high acetylenic hydrocarbons content. It is thus possible not only to treat a crude charge directly issued from a steam-cracking plant but also a mixture of said charge with an acetylenic concentrate withdrawn from a butadiene separation unit. In this case, the vinyl acetylene content at the inlet of the hydrogenation reactor may reach 1 to 10% by weight, the 1,3-butadiene content being, for example, from 30 to 70% by weight.

The process of the invention comprises the hydrogenation of the cut to be treated, at least partly in liquid phase, over a supported catalyst containing palladium and silver or their compounds, the palladium content by weight being from 0.05 to 0.5% (preferably from 0.1 to 0.4%), the silver content by weight from 0.05 to 1% (preferably from 0.1 to 0.5%) and the ratio by weight Ag/Pd being at least equal to 0.7, for example from 0.8 to 5.

The French Pat. No. 2036991 recommends silver contents comprised between 0.01 and 0.5 times the palladium content. These values do not provide a catalyst having a sufficient stability for the treatment of charges containing 1% by weight or more of acetylenic hydrocarbons.

Examples of carriers are alumina, silica, magnesia, a zeolite or a silicate or aluminosilicate.

The incorporation of palladium and silver compounds to the carrier may be effected by any one of the known methods. It can be achieved, for example, by impregnation of a preshaped or unshaped carrier by means of a common solution of compounds of the metals to be introduced, or of separate solutions, for example an aqueous solution containing soluble palladium salts such as palladium nitrate or chloride and a solution of soluble silver salts such as silver nitrate.

The metals, palladium and silver, may be incorporated simultaneously or successively. Between these two operations, a drying and calcination treatment may be effected. The catalyst, impregnated with the two metals, is then dried to remove the major part of the impregnation solvent and is finally calcined in air at a temperature from 200° to 900° C.

If necessary, a final reduction treatment can be effected by means of, for example, hydrogen, according to a known technique. The reduction temperature is preferably from 0° to 200° C. The reduction may also be effected by other methods, for example by means of hydrazine.

The carrier is preferably an alumina of a specific surface lower than 100 m2/g, for example I to 50 m2/g, having preferably a low acidity.

The hydrogenation conditions are those conventionally used for the selective hydrogenation of acetylenic hydrocarbons in the presence of butadiene, i.e. a temperature from 0° to 80° C., a pressure from 3 to 20 bars, selected sufficiently high to maintain the liquid phase, and a flow rate of the C4 out from 2 to 50 volumes per volume of catalyst and per hour. The molar ratio hydrogen/acetylenic hydrocarbons is in most cases from 1 to 5 i.e. 1:1 to 5:1, respectively.

The following examples illustrate the invention:

EXAMPLE 1 (comparative)

A catalyst is prepared by impregnation, with a nitric acid solution of palladium nitrate, of an alumina carrier, in balls of a 2 mm diameter, having a specific surface of 10 m2/g and a total pore volume of 96 cc/g, so as to obtain a final catalyst having a 0.3% by weight palladium content. After impregnation, the catalyst is dried at 120° C. in a stove ad then calcined at 450° C. for two hours in an air stream.

The catalyst is charged into a tubular reactor and reduced in situ by a hydrogen stream at 150° C. for two hours.

The charge to be treated has the following composition:

| Compound | % mole |
|---|---|
| Isobutane | 0.21 |
| Propylene | 0.05 |
| n butane | 0.53 |
| 1 - butene | 12.70 |
| Isobutene | 19.30 |
| Trans 2 - butene | 4.18 |
| Cis 2 - butene | 3.30 |
| 1,3 - butadiene | 57.32 |
| 1,2 - butadiene | 0.25 |
| 1 - butyne | 0.21 |
| Vinylacetylene | 1.95 |
| TOTAL | 100% |

The operating conditions are as follows:
Space velocity: 20 (vol/vol/h)
Total pressure: 6 bars
Temperature: 40° C.
H2/acetylenic hydrocarbons ratio: 1.2 mole/mole
In these conditions, the C4 cut is essentially in liquid phase.

The results obtained in relation with the test duration are summarized in Table I.

TABLE I

| Time in hours | Vinylacetylene content of the product in ppm by weight | I - butyne content of the product in ppm by weight |
|---|---|---|
| 50 | 330 | 500 |
| 140 | 990 | 950 |
| 720 | 2475 | 1300 |

It is desired to obtain a product containing less than 1000 ppm of vinyl acetylene. It can be seen that this performance is only achieved during 140 hours. The test is however continued for 720 hours.

The catalyst is then withdrawn from the reactor and it is observed that it contains no more than 0.12% by weight of palladium instead of the initial 0.3%. Moreover, it contains about 4.6% by weight of carbon resulting from the deposit of polymers.

EXAMPLE 2 (according to the invention)

A catalyst is prepared by impregnation, with a solution of palladium nitrate and silver nitrate, of an alumina carrier identical to that of Example 1. The catalyst is dried and then calcined as in Example 1 and contains 0.3% by weight of palladium and 0.3% by weight of silver.

The catalyst is then charged into a tubular reactor and reduced as in Example 1. The charge and the operating conditions of the test are the same as in Example 1. The results are summarized in Table II.

TABLE II

| Time in hours | Vinylacetylene content of the product in ppm by weight | I - butyne content of the product in ppm by weight |
|---|---|---|
| 50 | 250 | 500 |
| 720 | 330 | 540 |

It is observed that the catalyst according to the invention maintains its activity substantially unchanged during the test.

The catalyst withdrawn from the reactor contains 0.29% by weight of palladium in proportion to alumina, which corresponds, with the tolerance in the analysis accuracy, to the starting concentration. Moreover, the silver content is unchanged. The used catalyst contains about 2% by weight of deposit, calculated as carbon.

EXAMPLE 3 (comparative)

A catalyst is prepared, as in Example 2, with a 0.3% by weight palladium content but a silver content of only 0.15% by weight.

The catalyst is then charged into a tubular reactor, reduced as in Example 1 and tested under the same conditions. The results are summarized in Table III.

TABLE III

| Time in hours | Vinylacetylene content of the product in ppm by weight | I - butyne content of the product in ppm by weight |
|---|---|---|
| 50 | 300 | 500 |
| 720 | 2200 | 1100 |

The catalyst withdrawn from the reactor contains 0.20% by weight of palladium instead of the initial 0.3%. The deposit, calculated as carbon, is about 3% by weight. The catalyst is hence clearly less stable that the catalyst of Example 2, thus making obvious the importance of the ratio Ag/Pd.

EXAMPLE 4

A catalyst is prepared as in Example 2 with a 0.1% by weight palladium content and a 0.3% by weight silver content. The catalyst is then charged into a tubular reactor, reduced as in Example 1 and tested under the following operating conditions:
Space velocity: 10 (vol/vol/h)
Total pressure: 6 bars
Temperature: 40° C.
H2/acetylenic hydrocarbons ratio: 1.2 mole/mole
The C4 cut is in liquid phase.

The space velocity in this Example is 10 instead of 20 in the preceding Examples since the initial activity of this catalyst of low palladium content is lower.

The results obtained in relation with the test duration are summarized in Table IV.

TABLE IV

| Time in hours | Vinylacetylene content of the product in ppm by weight | I - butyne content of the product in ppm by weight |
| --- | --- | --- |
| 50 | 400 | 600 |
| 720 | 450 | 620 |

The catalyst withdrawn from the reactor contains 0.1% by weight of palladium and 0.28% by weight of silver.

EXAMPLE 5

The catalysts of the above Examples 1 and 2 are used comparatively for hydrogenating a cut of high vinylacetylene content.

The charge to be treated has the following composition:

| Compound | Mole % |
| --- | --- |
| Butanes | 7 |
| Isobutene | 18.6 |
| I - butene | 12.2 |
| Trans 2 - butene | 4 |
| Cis 2 - butene | 3.2 |
| 1,3 - butadiene | 48.9 |
| 1,2 - butadiene | 1.4 |
| Vinylacetylene | 4.1 |
| I - butyne | 0.6 |
| Total | 100% |

This cut is obtained by dilution of the acetylenic fraction obtained by solvent extraction from a steam-cracking butadiene cut, said fraction having a vinylacetylene content of about 30% by weight; the dilution is effected with a portion of the crude butadiene cut charged in the extraction unit.

The operation is conducted in the liquid phase under the following conditions:

Space velocity: 20
Total pressure: 6 bars
Temperature: 40° C.
Hydrogen/acetylenic compounds ratio: variable At the beginning of the test this ratio is set to 1 but is progressively increased when the catalyst deactivates, in order to maintain at a constant value of 1% by weight the vinylacetylene content of the product. The results are reported in Tables V and VI.

TABLE V

| | Catalyst of example 1 | |
| --- | --- | --- |
| Time in hours | H$_2$/acetylenics ratio necessary to maintain the conversion rate | Yield* of 1,3 butadiene |
| 50 | 1 | 104% |
| 720 | 4 | 96% |

*Yield of 1,3 butadiene = $\frac{\% \text{ BD in the product}}{\% \text{ BD in the charge}} \times 100$ The catalyst, withdrawn from the reactor after 720 hours, only contains 0.04% by weight of palladium instead of the initial 0.3%. The butadiene yield falls significantly to a level clearly below 100%.

TABLE VI

| | Catalyst of example 2 | |
| --- | --- | --- |
| Time in hours | H$_2$/acetylenics ratio necessary to maintain the conversion rate | Yield of 1,3 butadiene |
| 50 | 1 | 104% |
| 720 | 1.2 | 102% |

The catalyst, withdrawn from the reactor after 720 hours, contains 0.27% of palladium and its silver content is maintained at its initial value. The yield to butadiene is maintained at a level substantially above 100%.

We claim:

1. In a process for the selective catalytic hydrogenation of the acetylenic hydrocarbons of a C$_4$ hydrocarbon cut containing a substantial quantity of butadiene and at least 1% by weight of acetylenic hydrocarbons, without substantial hydrogenation of butadiene, wherein said hydrocarbon cut in the liquid phase and hydrogen are contacted with a supported catalyst under hydrogenation conditions selective for hydrogenating said acetylenic hydrocarbons without substantial hydrogenation of butadiene, the improvement wherein said supported catalyst consists essentially of a carrier, 0.05 to 0.5% by weight of palladium and 0.05 to 1% by weight of silver, with the further provision that the Ag/Pd ratio by weight is at least 0.7, thus increasing the life of the selectivity of the catalyst.

2. A process according to claim 1 wherein said Ag/Pd ratio is from 0.8 to 5.

3. A process according to claim 1 or 2, wherein the catalyst carrier is an alumina of a surface from 1 to 50 m2/g.

4. A process according to claim 1 or 2, wherein the C$_4$ cut contains from 30 to 70% by weight of 1,3-butadiene and from 1 to 10% by weight of vinylacetylene.

5. A process according to claims 1 or 2, wherein the palladium content by weight is from 0.1 to 0.5% and the silver content by weight from 0.1 to 0.5%.

6. A process according to claim 1, wherein the hydrogenation conditions are: a temperature of 0° to 80° C., a pressure of 3 to 20 bars, and a flow rate of 2 to 50 volumes of C$_4$ cut per volume of catalyst per hour.

7. A process according to claim 1 or claim 6, wherein the molar ratio of hydrogen:acetylenic hydrocarbons is 1:1 to 5:1, respectively.

8. A process according to claim 1, wherein said Ag/Pd ratio is at least 1.

* * * * *